United States Patent [19]

Stewart

[11] Patent Number: 5,166,340
[45] Date of Patent: Nov. 24, 1992

[54] ORGANOSILANE COMPOUNDS

[75] Inventor: Constantine A. Stewart, Wilmington, Del.

[73] Assignee: Himont Incorporated, Wilmington, Del.

[21] Appl. No.: 573,618

[22] Filed: Aug. 27, 1990

Related U.S. Application Data

[63] Continuation-in-part of Ser. No. 386,183, Jul. 26, 1989, abandoned.

[51] Int. Cl.$^5$ .............................. C07F 7/02; C07F 7/10; C08F 4/16
[52] U.S. Cl. ...................................... 540/450; 540/609; 548/406; 546/14
[58] Field of Search ....................... 546/14; 548/406; 540/450, 609

[56] References Cited

U.S. PATENT DOCUMENTS

| | | | |
|---|---|---|---|
| 4,347,160 | 8/1982 | Epstein et al. | 252/429 B |
| 4,382,019 | 5/1983 | Greco | 252/429 B |
| 4,435,550 | 3/1984 | Ueno et al. | 526/73 |
| 4,465,782 | 8/1984 | McKenzie | 502/104 |
| 4,472,524 | 9/1984 | Albizzati | 502/113 |
| 4,473,660 | 9/1984 | Albizzati et al. | 502/124 |
| 4,522,930 | 6/1985 | Albizzati et al. | 502/124 |
| 4,530,912 | 7/1985 | Pullukat et al. | 502/104 |
| 4,560,671 | 12/1985 | Gross et al. | 502/105 |
| 4,581,342 | 4/1986 | Johnson et al. | 502/119 |
| 4,657,882 | 4/1987 | Karayannis et al. | 502/115 |
| 4,663,314 | 5/1987 | Hayase et al. | 546/14 |
| 4,804,653 | 2/1989 | Strunk et al. | 546/14 |

FOREIGN PATENT DOCUMENTS

| | | | |
|---|---|---|---|
| 0045976 | 2/1982 | European Pat. Off. | 556/412 |
| 0045977 | 2/1982 | European Pat. Off. | 556/412 |

OTHER PUBLICATIONS

Royals "Advanced Organic Chemistry" (Prentice Hall) (1954) pp. 188-189.

Primary Examiner—Robert T. Bond

[57] ABSTRACT

Organosilane compounds having the structural formula

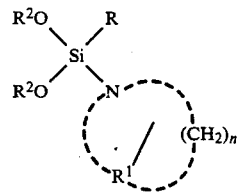

wherein R is a linear or branched $C_{1-4}$ alkyl, 4-methylpiperidyl, $C_{6-12}$ aryl or $C_{5-7}$ cycloalkyl; $R^1$ is hydrogen, methyl or ethyl; $R^2$ is methyl or ethyl and; n is 4 to 7.

These organosilane compounds are useful as electron donors in Ziegler-Natta type catalyst systems.

12 Claims, No Drawings

ORGANOSILANE COMPOUNDS

This application is a continuation-in-part of U.S. patent application Ser. No. 386,183, filed Jul. 26, 1989, now abandoned.

Field of the Invention

This invention relates to a new class of organosilane compounds for use as an electron donor in Ziegler-Natta supported catalyst systems, particularly for such catalyst systems having an anhydrous activated $MgCl_2$ as the support, for the polymerization of alpha-olefins.

BACKGROUND OF THE INVENTION

Electron donor compounds, also known as Lewis Bases, have been widely used in catalyst systems (1) as an electron donor in the solid component of the catalyst system comprising a halogen-containing Ti compound supported on an anhydrous activated Mg dihalide compound and (2) as an electron donor with the co-catalyst component comprising an organometallic compound, to increase the activity and stereospecificity of the catalyst for the polymerization of alpha-olefins, in particular propylene and higher alpha-olefins.

Conventional classes of electron donor compounds known in the art include ethers, ketones, amines, alcohols, phenols, phosphines and silanes. Examples of such electron donor compounds and their use as a component of the catalyst system are described in U.S. Pat. Nos. 4,107,414, 4,186,107, 4,226,963, 4,347,160, 4,382,019, 4,435,550, 4,465,782, 4,472,524, 4,473,660, 4,522,930, 4,530,912, 4,532,313, 4,560,671, and 4,657,882.

Electron donors consisting of organosilane compounds, containing Si—OCOR, Si—OR, or Si—$NR_2$ bonds, having silicon as the central atom, and R is an alkyl, alkenyl, aryl, arylalkyl or cycloalkyl with 1-20 carbon atoms are known in the art. Such compounds are described in U.S. Pat. Nos. 4,347,160, 4,382,019, 4,435,550, 4,465,782, 4,473,660, 4,530,912 and 4,560,671 where they are used as an electron donor in the solid catalyst component; and U.S. Pat. Nos. 4,472,524, 4,522,930, 4,560,671, 4,581,342 4,657,882 and European Patent applications 45976 and 45977 where they are used as an electron donor with the co-catalyst.

However, in all of the above catalyst systems in which an organosilane compound is used, none describe organosilane compounds containing Si—N bonds where the nitrogen bonded to the silicon atom is a nitrogen of a nitrogen containing heterocyclic ring.

SUMMARY OF THE INVENTION

The present invention provides a new class of organosilane compounds containing a Si-N bond, wherein the nitrogen is a 5-8 membered nitrogen containing heterocyclic ring. These compounds are used as an electron donor with the co-catalyst component of supported Ziegler-Natta catalyst systems for polymerization of alpha-olefins. Using the new compounds of the present invention in such catalyst systems result in catalysts of increased activity and stereospecificity.

BRIEF DESCRIPTION OF THE INVENTION

The new class of organosilane compounds have the following structure:

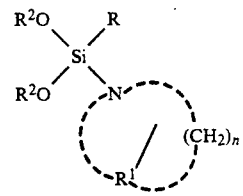

where R is a $C_{1-4}$ linear or branched alkyl, 4-methylpiperidine, $C_{6-12}$ aryl or $C_{5-7}$ cycloalkyl; $R^1$ is hydrogen, methyl or ethyl; $R^2$ is methyl or ethyl and; n is 4 to 7.

Examples of linear or branched alkyl include methyl, ethyl, isopropyl and tert-butyl.

Examples of aryl include phenyl and phenyl substituted in the para position with halogen, $C_{1-4}$ linear or branched alkyl or $C_{1-4}$ alkoxy.

Examples of cycloalkyl include cyclopentane, cyclohexane, and bicycloheptane.

Typical organosilane compounds are: t-butyl(4-methylpiperidyl)dimethoxysilane, t-butyl(3-methylpiperidyl)dimethoxysilane, t-butyl(2-methylpiperidyl)dimethoxysilane, bis(4-methylpiperidyl)dimethoxysilane, 2-bicycloheptyl(4-methylpiperidyl)dimethoxysilane, isopropyl(4-methylpiperidyl)dimethoxysilane, n-butyl(4-methylpiperidyl)dimethoxysilane and isobutyl(4-methylpiperidyl)dimethoxysilane.

It has been found that the new organosilane compounds of the present invention when used as an electron donor with the co-catalyst or activator in supported catalyst systems provide further control over the polymerization of alpha-olefins. It is known in the art that the use of electron donors with the co-catalyst provide an increase in the activity of supported catalysts and control of stereospecificity and molecular weight. When so used, the organosilane compounds of the present invention containing a Si—N bond, wherein the nitrogen is a 5-8 membered nitrogen containing heterocyclic ring and the non-alkoxy substituent, R, is of sufficient size to provide steric hindrance, have a significant effect on the aforementioned activities of the catalyst and properties of the polymer produced therefrom over the conventional organosilane compounds containing Si—OR or Si—OCOR or Si—$NR_2$ bonds, where R is alkyl, aryl, alkenyl or arylalkyl, when used in a like manner.

The success of the new organosilane compounds of the present invention as electron donors appears to be attributed to various factors such as the size of the R group attached directly to the central silicon atom wherein the more sterically demanding the R group is, the greater the increase in activity and stereospecificity of the catalyst. In other words, as the R group increases in size there is an increase in mileage (grams of polypropylene/grams of catalyst) and stereospecificity. There is a limit to the size of the R group attached to the silicon atom in which benefits of increased activity and stereospecifity are realized. Excessive steric bulk results in a reduced activity and a decrease in stereospecificity, which is manifested by an increase in xylene solubles.

The presence of the nitrogen containing heterocyclic ring bonded directly to the silicon atom through the nitrogen is also a factor. It appears that the Si-N bond contributes to the decrease in xylene soluble polymer and in some cases an increase in intrinsic viscosity (IV).

In addition to the above factors, it appears that the presence of two alkoxy groups directly attached to the silicon atom also contributes to an increase in stereospecificity and mileage as compared to organosilane donor compounds containing only one alkoxy group.

It is believed that the combination of the above factors contribute to the high IV polymers while still retaining high stereospecificity and mileage when the organosilane compounds of the present invention are used with the co-catalyst component.

As a general rule the concentration of the organosilane effects the activity and stereospecificity of the catalyst and the intrinsic viscosity of the polymer. It is known in the art that concentration effects of the donor vary from donor to donor. Surprisingly, the organosilanes of the present invention as electron donors with the aluminum-alkyl co-catalyst can be used in lower concentrations than the conventional electron donors with the aluminum-alkyl co-catalyst and still give very good stereoregulating control and increase in activity.

The organosilane compounds of the present invention are used as a component in the Ziegler-Natta type catalyst system comprising the reaction product of (A) an Al-alkyl compound, (B) an organosilane compound of the present invention and (C) a solid catalyst forming component comprising a Ti compound having at least a Ti-halogen bond and an electron donor compound supported on an anhydrous Mg-dihalide in active form.

The amount of the organosilane compound is preferably such that at least 10% of the Al-alkyl compound is in the form of a complex with the organosilane compound of the present invention.

The Al-alkyl compounds forming component (A) include Al-trialkyls such as, Al triethyl, Al triisobutyl, Al triisopropyl, Al-dialkyl hydrides, such as Al-diethyl hydrides, and compounds containing two or more Al atoms linked to each other through hetero-atoms, such as:

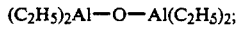

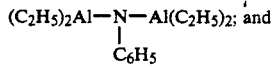

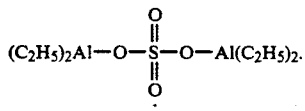

In the solid catalyst forming component (C), suitable examples of the Ti compound having at least a Ti-halogen bond employed in component (C) are Ti tetrahalides, in particular, $TiCl_4$. However, alkoxy halides can also be used.

The electron donor compounds for preparing component (C) include alkyl, aryl and cycloalkyl esters of aromatic acids, in particular the alkyl esters of benzoic acid and phthalic acid and their derivatives. Specific examples include ethyl benzoate, n-butyl benzoate, methyl-p-toluate, methyl-pmethoxybenzoate and diisobutylphthalate. In addition to the above esters, alkyl or alkyl-aryl ethers, ketones, mono- or polyamines, aldehydes and P-compounds, such as phosphines and phosphoramides can also be used as the electron donor.

The active anhydrous Mg dihalides forming the support of component (C) are the Mg dihalides showing in the X-ray powder spectrum of component (C) a broadening of at least 30% of the most intense diffraction line which appears in the powder spectrum of the corresponding dihalide having 1 $m^2/g$ of surface area or are the Mg dihalides showing an X-ray powder spectrum in which said most intense diffraction line is replaced by a halo with the intensity peak shifted with respect to the interplanar distance of the most intense line and/or are the Mg dihalides having a surface area greater than 3 $m^2/g$.

The measurement of the surface area of the Mg dihalides is made on component (C) after treatment with boiling $TiCl_4$ for 2 hours. The found value is considered as surface area of the Mg dihalide.

The Mg dihalide may be preactivated, may be activated in situ during the titanation, may be formed in situ from a Mg compound, which is capable of forming Mg dihalide when treated with a suitable halogen-containing transition metal compound, and then activated, or may be formed from a Mg dihalide. $C_{1-8}$ alkanol adduct wherein the molar ratio of $MgCl_2$ to alcohol is 1:1 to 1:3, such a $MgCl_2 \cdot 3ROH$.

Very active forms of Mg dihalides are those showing an X-ray powder spectrum in which the most intense diffraction line appearing in the spectrum of the corresponding halide having 1 $m^2/g$ of surface area is decreased in relative intensity and broadened to form a halo or are those in which said most intense line is replaced by a halo having its intensity peak shifted with respect to the interplanar distance of the most intense line. Generally, the surface area of the above forms is higher than 30–40 $m^2/g$ and is comprised in particular between 100–300 $m^2/g$.

Active forms are also those deriving from the above forms by heat-treatment of component (C) in inert hydrocarbon solvents and showing in the X-ray spectrum sharp diffraction lines in place of the halos. The sharp, most intense line of these forms shows, in any case, a broadening of at least 30% with respect to the corresponding line of the Mg dihalide having 1 $m^2/g$ of surface area.

Preferred Mg dihalides are Mg dichloride and Mg dibromide. The content in water of the dihalides is generally less than 1% by weight.

By Ti halides or Ti alkoxy halides and electron donors supported on active Mg dihalide is meant the above compounds which may be chemically or physically fixed on the support, and not extractable from component (C) by treatment of the same with boiling, 1,2-dichloroethane for 2 hours.

Component (C) can be made by various methods. One of these methods consist of co-grinding the Mg dihalide and the electron donor compound until the product, after extraction with Al-triethyl under standard conditions, shows a surface area higher than 20 $m^2/g$, as set forth above for the spectrum of the Mg dihalide, and thereafter reacting the ground product with the Ti compound.

Other methods of preparing the solid catalyst forming component (C) are disclosed in U.S. Pat. Nos. 4,220,554, 4,294,721, 4,315,835, and 4,439,540. The methods of which are incorporated herein by reference.

In all of the above methods, component (C) contains a Mg dihalide present in the active form as set forth above.

Other known methods which lead to the formation of Mg dihalide in active form or to Ti-containing Mg dihalide supported components, in which the dihalide is present in active form, are based on the following reactions:

(i) reaction of a Grignard reagent or $MgR_2$ compound (R being a hydrocarbyl radical) or complexes of said $MgR_2$ compounds with Al trialkyl, with halogenating agents as $AlX_3$ or $AlR_mX_n$ compounds (X is halogen, R is a hydrocarbyl, m+n=3), $SiCl_4$ or $HSiCl_3$;

(ii) reaction of a Grignard reagent with a silanol or polysiloxane, $H_2O$ or with an alcohol and further reaction with a halogenating agent or with $TiCl_4$;

(iii) reaction of Mg with an alcohol and a halogenhalide acid, or of Mg with a hydrocarbyl halide and an alcohol;

(iv) reaction of MgO with $Cl_2$ or $AlCl_3$;

(v) reaction of $MgX_2 \cdot nH_2O$ (X=halogen and n is 1-3) with a halogenating agent or $TiCl_4$; or (vi) reaction of Mg mono or dialkoxides or Mg carboxylates with a halogenating agent.

In component (C), the molar ratio between the Mg dihalide and the halogenated Ti compound supported thereon is between 1 and 500 and the molar ratio between said halogenated Ti compound and the electron donor supported on the Mg dihalide is between 0.1 and 50.

The catalyst, i.e., components (A), (B) and (C) can be added to the polymerization reactor by separate means substantially simultaneously, regardless of whether the monomer is already in the reactor, or sequentially if the monomer is added to the polymerization reactor later. It is preferred to premix components (A) and (B), then contact said premix with component (C) prior to the polymerization for from 3 minutes to about 10 minutes at ambient temperature.

The olefin monomer can be added prior to, with or after the addition of the catalyst to the polymerization reactor. It is preferred to add it after the addition of the catalyst.

Hydrogen can be added as needed as a chain transfer agent for reduction in the molecular weight of the polymer.

The polymerization reactions can be done in slurry, liquid or gas phase processes, or in a combination of liquid and gas phase processes using separate reactors, all of which can be done either by batch or continuously.

The polymerization is generally carried out at a temperature of from 40°-90° C. and at atmospheric pressure or at higher pressure.

The catalysts may be precontacted with small quantities of olefin monomer (prepolymerization), maintaining the catalyst in suspension in a hydrocarbon solvent and polymerizing at a temperature of 60° C. or below for a time sufficient to produce a quantity of polymer from 0.5 to 3 times the weight of the catalyst.

This prepolymerization also can be done in liquid or gaseous monomer to produce, in this case, a quantity of polymer up to 1000 times the catalyst weight.

Suitable alpha-olefins which can be polymerized by this invention include olefins of the formula $CH_2=CHR$, where R is H or $C_{1-10}$ straight or branched alkyl, such as ethylene, propylene, butene-1, pentene-1, 4-methylpentene-1 and octene-1.

The following examples are shown to illustrate the invention and are not intended to define the scope thereof.

All solvents were freshly dried and distilled and stored over activated molecular sieves under an inert atmosphere, prior to use.

Analysis of the silane compounds by $^1H$ NMR and $^{13}C$ NMR spectra were recorded on a Varian EM-390 and a Nicolent NT-360WB, respectively, using $CDCl_3$ as a solvent and $Me_4Si$ as a reference. All NMR spectra are reported in ppm.

Analysis of the silane compounds by gas chromatography mass spectrometry (GC-MS) were recorded on a Hewlett-Packard Model 5890 Gas Chromatograph linked with a model 5970 Mass Selective Detector and a Series 300 Chemstation for integration and data handling. The column was a H-P 1 Ultra fused silica capillary column, 30 m x 0.2 mm with a 0.18 micron film thickness. The chromatographic conditions were as follows: GC injector temperature of 100° C.; transfer line temperature of 250° C.; GC oven program set at 75° C. to 250° C. at 6 deg. per minute, held at 250° C. for 15 minutes; carrier gas (helium) flow rate of 0.6 ml/min., a split flow rate of 40 ml/min.; and an injection volume of 0.1 microliter. The scan range for the MS was 10 to 600 amu. The mass spectra were obtained from the Total Ion chromatogram after the GC had been completed.

The alkyl lithium reagents were titrated for total lithium content by using HCl and a phenolphthalein indicator.

Unless otherwise indicated, all reactions were conducted under an inert atmosphere, using a mercury bubbler.

EXAMPLE 1

This example illustrates an organosilane compound of this invention and a method of preparing the same.

(a) To a reaction vessel fitted with a reflux condenser and purged with argon was added 200 ml of Ar purged methanol. The vessel was cooled to 0° C. in an ice bath. Then charged with 3.5 g (0.504 mol) of lithium ribbon that had been cut into small pieces and added to the methanol over a period of 1.5 hrs. After the addition was complete, the reaction mixture was allowed to warm to room temperature (approx. 3° C.), then the mixture was refluxed for 3 hrs. A cloudy, slightly yellow viscous solution resulted. The solution was filtered through a medium porosity frit, using Celite diatomaceous earth as a filter aid. The clear, light yellow solution was titrated with HCl and phenolphthalein to give a 2.76 M solution of methoxy-lithium/methanol.

(b) Under argon, a reaction vessel fitted with a funnel and stirrer was charged with 200 ml diethylether and 7.3 ml 4-methylpiperidine (0.0615 mol), and stirring commenced. Through the funnel, 32.4 ml n-butyllithium/hexane solution (1.9 M) was added over 1 hr. and stirring of the reaction contents was continued for about 2 more hours. A 0.30 M solution of 1-lithio-4-methylpiperidine in diethylether was obtained.

(c) Under argon, a reaction vessel fitted with a stirrer was charged with 100 ml diethylether and 11.7 g. t-butyltrichlorosilane (0.0615 mol) and stirring was commenced. To this vessel was added dropwise 6.34 g 1-lithio-4-methylpiperidine in diethylether solution from (b) above via a cannula over a 30 min. period and stirring was continued for about 16 hours. The vessel was fitted with a condenser and the reaction mixture was refluxed for 1 hr. and cooled to room temperature. The solution was filtered through a medium porosity frit and the LiCl precipitate was washed three times with 20 ml portions of diethylether. The diethylether was removed from the filtrate in vacuo to provide a clear yellow oil. The crude product was distilled under vacuum (60°-68° C., @ 0.7 torr) to give a clear to slightly cloudy oil of 6.45 g of t-butyl(4methylpiperidyl)dichlorosilane.

(d) Under argon, a reaction vessel was charged with 200 ml THF and 6.45 g t-butyl(4-methylpiperidyl)dichlorosilane (0.0254 mol) obtained from (c) above. To this solution was added 18.4 ml of a 2.76 M MeOLi/MeOH solution (0.0508 mol MeOLi) from step (a) dropwise via a cannula over a 30 min. period and the mixture was refluxed for 2 hrs. The reaction was allowed to cool to room temperature and the solvents stripped under vacuum to give an oil containing a white precipitate. The oil was extracted in hexane and the hexane removed under vacuum to give a clear, colorless oil. The oil was distilled under vacuum (46°–49° C., @ 0.7 torr) to yield 4 ml of a clear, colorless oil, of t-butyl(4-methylpiperidyl)- dimethoxysilane $^1$H NMR (CDCl$_3$) δ0.9 (d,1H), 1.0 (s,9H), 1.5 (m,3H), 2.6 (m,4H), 3.2 (m,4H), 3.5 (s,6H), $^{13}$C$^1$H (CDCl$_3$) 19.1 (C(CH$_3$)$_3$),22.7 (CH$_3$ ring), 26.6 (C(CH$_3$)$_3$), 31.8 (CH), 36.1 (CH$_2$), 45.7 (CH$_2$), 50.7 (OCH$_3$).

EXAMPLES 2 to 4

The procedure and ingredients of example 1 were repeated with the following exceptions shown in Table 1.

diethylether. The ether was removed in vacuo to afford a pale yellow oil. The product was distilled at 101° C., atmospheric pressure, to give a clear, colorless liquid of 2.39 g of dimethoxydichlorosilane.

(b) Under argon, a reaction vessel was charged with 100 ml of diethylether and 2.3 g dimethoxydichlorosilane (0.014 mol) in ether. To this solution was added dropwise a solution of 1-litho-4-methylpiperidine in diethylether of example 1 (b) (0.028 mol) in ether. The reaction mixture was refluxed for 6 hrs. then cooled to room temperature. The solid was removed by filtration and the ether stripped off under vacuum. The crude product was distilled under vacuum (84° C.,@.0.9 torr) to yield 4 ml of bis(4-methylpiperidyl)-dimethoxysilane, a clear, colorless oil. $^1$H NMR (CDCl$_3$) δ 1.0 (d,1H), 1.1 (s,3H), 1.3 (m,2H), 2.5 (m,2H), 3.0 (m,4H), 3.4 (s,3H).

EXAMPLE 6

Under nitrogen, a reaction vessel was charged with 150 ml diethylether and 33 ml 4-methylpiperidine (0.026 mol) and cooled to 0° C. in an ice bath while stirring. The vessel was adapted with an addition funnel which was charged with 11 ml n-butyllithium (0.026 mol) and

TABLE 1

| Example | Process Step | Ingredients | Amounts | Intermediate Product | Final Product |
| --- | --- | --- | --- | --- | --- |
| 2 | (b) | 3-Methylpiperidine<br>n-Butyllithium/hexane solution | 7.2 ml (0.0616 mol)<br>24.6 ml (2.5M) | 1-Litho-3-methylpiperidyl-<br>diethylether (6.31 g, 0.0600 mol) | |
| | (c) | t-Butyltrichlorosilane<br>Intermediate product obtained from step (b) | 11.7 g (0.0616 mol)<br>6.31 g (0.0600 mol) | t-Butyl-3-methylpiperidyl-<br>dichlorosilane (11.8 g, 0.0464 mol) | |
| | (d) | Intermediate product obtained from step (c)<br><br>MeOLi/MEOH | 11.8 g (0.0464 mol)<br><br>34.5 ml (2.69M)<br>(0.0928 mol MeOLi) | | 9 ml t-Butyl-<br>(3-methylpiper-<br>idyl)dimethoxy-<br>silane |
| 3 | (b) | 2-Methylpiperidine<br>n-Butyllithium/hexane solution | 6.96 ml (0.0590 mol)<br>23.7 ml (2.5M) | 1-Litho-2-methylpiperidyl-<br>diethylether (6.10 g, 0.058 mol) | |
| | (c) | t-Butyltrichlorosilane<br>Intermediate product obtained from step (b) | 11.3 g (0.0590 mol)<br>6.10 g (0.058 mol) | t-Butyl-2-methylpiperidyl-<br>dichlorosilane (11.6 g, 0.0456 mol) | |
| | (d) | intermediate product obtained from step (c)<br><br>MeOLi/MeOH | 11.6 g (0.0456 mol)<br><br>33.8 ml (2.69M)<br>(0.0910 mol MeOLi) | | 9 ml t-Butyl-<br>(2-methylpiper-<br>idyl)dimethoxy-<br>silane |
| 4 | (c) | Diethylether<br>2-Bicycloheptyltrichlorosilane<br>1-Lithio-4-methylpiperidyl-<br>diethylether | 200 ml<br>13.5 g (0.059 mol)<br>6.2 g (0.059 mol) | 2-Bicycloheptyl-<br>(4-methylpiperidyl)-<br>dichlorosilane (4.4 g, 0.15 mol) | |
| | (d) | Diethylether<br>Intermediate product obtained from step (c) above<br><br>MeOLi/MeOH | 300 ml<br>4.4 g (0.15 mol)<br><br>68.2 ml (0.030 mol, 0.44M) | | 1.4 g 2-Bicyclo-<br>heptyl(4-methyl-<br>piperidyl)-<br>dimethoxysilane |

EXAMPLE 5

(a) Under argon, a reaction vessel fitted with a funnel and stirrer, the vessel was charged with 250 ml of diethylether and 12 ml SiCl$_4$ (0.105 mol) and while stirring was cooled to 0° C. in an ice bath. Then the funnel was charged with 80 ml of ether, 8.9 ml MeOH (0.291 mol, 5% molar excess) and 27.3 ml NEt$_3$ (0.291 mol, 5% molar excess) which were added over a period of about 2 hrs. at which time the formation of triethylamine hydrochloride occurred. An extra 100 ml, of diethylether was added to facilitate stirring. The stirring of the reaction mixture continued for about 16 hours at room temperature. The solution was filtered and the amine hydrochloride washed 3 times with 20 ml of 50 ml hexane. The hexane/nbutyllithium butyllithium solution was added dropwise to the reaction mixture and the reaction mixture was stirred for an additional hour at 0° C. at which time the ice bath was removed and the contents of the flask were allowed to warm to room temperature. After warming to room temperature, stirring was continued for an additional hour and 2.68 g 1-lithio-4-methylpiperidine was obtained.

In a separate reaction vessel under nitrogen, 5.0 ml n-butyl(trimethoxy)silane (0.026 mol.) was added along with 50 ml hexane. The vessel was cooled to 0° C. in an ice bath while stirring. To the cooled n-butyl(trimethoxy)silane/hexane solution obtained was added, via cannula, 2.68 g 1-lithio-4-methylpiperidine suspension from the first vessel. After the addition was completed, the reaction mixture was allowed to warm to room temperature, stirred for about 16 hours, then heated to reflux for about 2 hours. The solvents were then removed in vacuo and the white solid was washed 3 times with 20 ml portions of hexane to remove the product. The hexane was stripped from the product under vacuum to give an oil.

The oil was distilled on a long path column under vacuum (47° C., 0.5 mm Hg) to give 4.6 g of n-butyl(4-methylpiperidyl)dimethoxysilane. GC analysis showed product to be 98.5% pure. GC-MS indicates the desired product, m/z=245, 34% abundance.

EXAMPLE 7

Under nitrogen, a reaction vessel was charged with 200 ml diethylether and 36.7 ml of a 1.5 M solution of isopropylmagnesium chloride (0.055 mol) then cooled to 0° C. in an ice bath while stirring. In a separate reaction vessel, 11.86 g 4-methylpiperidyl(trimethoxy)silane (0.054 mol) and 50 ml of hexane were mixed together. The 4-methylpiperidyl(trimethoxy)silane/hexane solution was added to the Grignard above via a cannula over a period of about 1.5 hours. The reaction mixture was then refluxed for about 2 hours.

The magnesium salts were filtered out by using a medium porosity frit and Celite diatomaceous earth. Dichloromethane (2.3 g, 0.027 mol) was added to the solution to react with the remainder of the Grignard. The reaction mixture was stirred and then allowed to settle for 2 hours. All of the solvents were removed in vacuo leaving a cloudy oil, which solidified overnight.

Hexane (75 ml) was added to the solid and dioxane (9.2 ml, 0.107 mol), the solution was stirred for 30 mins. and then filtered. The hexane was removed by vacuum pumping. The remaining oil was distilled on an extra long distillation column under reduced pressure to yield 3.5 g of a clear, colorless oil of isopropyl(4-methyl-piperidyl)dimethoxysilane collected at 45° C. (0.05 mm Hg). The GC analysis indicated 96.5% purity. GC-MS analysis showed a parent ion at 231.

EXAMPLE 8

A solution of 1-lithio-4-methylpiperidine (0.052 mol) was prepared as in step (b) of example 1. Under nitrogen, a reaction vessel flask was charged with 75 ml of hexane and 10 ml isobutyl(trimethoxy)silane (0.052 mol). While stirring, the vessel was then cooled to 0° C. and the 1-lithio-4-methylpiperidine was added dropwise via a cannula over a period of about 2.5 hours. The ice-bath was removed from the reaction vessel and the vessel was fitted with a nitrogen purged reflux condenser and the reaction mixture was refluxed for 2 hours, cooled to room temperature and stirred for about 16 hours.

The methoxylithium was filtered and the solvents were removed in vacuo. The resultant clear, yellow oil was distilled on a long path column under reduced pressure (0.06 mm Hg) at 40° C. to give 10.1 g of a clear, colorless oil of isobutyl(4-methylpiperidyl)dimethoxysilane (79% yield). The GC analysis indicated 93.1% purity.

The sample was redistilled using a long path column under reduced pressure again. After the head temperature reached 40° C. about 2 grams of product was allowed to pass, then the remaining fraction was collected. The GC analyis indicated 97% purity.

EXAMPLE 9

Under nitrogen, a reaction vessel was charged with 7.61 g t-butyl(pyrrolidyl)dichlorosilane (0.0335 mol) and 150 ml of tetrahydrofuran (THF) and cooled to 0° C. The vessel was adapted with an addition funnel that was charged with 24.5 ml methoxylithium (0.067 mol) which was then added dropwise to the reaction mixture. After the addition was complete, the solution was refluxed for two hours. THF was removed under vacuum until lithium chloride began to fall out of solution. Hexane (approx. 100 ml) was used to further extract the product from the lithium chloride. The mixture was then filtered under vacuum, and LiCl was washed a second time with approximately 100 ml hexane. The solution was filtered again under vacuum, and the solvent was also removed under vacuum. The product, a clear, pale green oil, was distilled under vacuum (0.01 torr), and 5.78 g of t-butyl(pyrrolidyl)dimethoxysilane was collected 28° C. GC analysis indicated 99.1% purity, GC-MS, m/z=217; calculated 217.38 amu.

EXAMPLE 10

Under a nitrogen, a reaction vessel was charged with 4.6 ml heptamethyleneimine (0.0368 mol) and 50 ml THF. The vessel was adapted with an addition funnel charged with 23.0 ml n-butyllithium (0.0368 mol) which was then added to the reaction vessel dropwise over a period of one hour.

A separate reaction vessel was charged with 5.3 ml methyltrimethoxysilane (0.0368 mol) and 50 ml of THF. 4.3 g heptamethyleneiminelithium in the THF solution prepared above was added to the methyltrimethoxysilane solution dropwise via a cannula over a one hour period. The resulting mixture was refluxed for two hours and then filtered under vacuum, using diatomaceous earth as a filtering aid. The solvent was removed from the filtrate under vacuum, leaving a clear, Yellow-green liquid. An attempt to extract methoxylithium in hexane 0° C. was unsuccessful. The crude product was distilled under vacuum (0.030 torr). A clear, colorless fraction was collected at 33°–35° C., of 4.27 g heptamethyleneimine(methyl)dimethoxysilane. GC analysis indicated 97.8% purity, GC-MS, m/z=217 amu; calculated 217.38 amu.

EXAMPLE 11

Under nitrogen, a reaction vessel was charged with 200 ml hexane and 2.10 ml piperidine (0.0177 mol) and cooled to 0° C. An addition funnel of the reaction vessel was charged with 11.06 ml n-butyllithium (1.6 M, 0.0177 mol) which was added dropwise to the mixture. After the addition was complete, the solution was stirred at room temperature for about one hour.

A second reaction vessel was charged with 3.15 g t-butyltrimethoxysilane (0.0177 mole) and 200 ml hexane. The t-butyltrimethoxysilane formed was added to the first reaction vessel dropwise via a cannula and refluxed for one hour. This solution was filtered under vacuum through a medium porosity frit, using diatomaceous earth as a filtering aid and 5.89 g of t-butyl(piperidyl)dimethoxysilane solids were obtained. The solvent was removed from the filtrate under vacuum (0.01 torr), and the product was purified through distillation. One fraction was collected at 78°–79° C. GC analysis indicated 98.7% purity; GC-MS, m/z=232 amu; calculated, 231.41 amu.

Polymerization of Propylene

The polymerization reactor was heated to 70° C. and purged with a slow argon flow for 1 hour. The reactor was then pressured up to 100 psig with argon at 70° C. and then vented; and this procedure was repeated 4 more times. The reactor was then pressured up to 100 psig with propylene and then vented; and this procedure was repeated 4 more times. The reactor was then cooled to 30° C.

Separately, into an argon purged addition funnel was introduced in the following order: 75 ml of hexane, 4.47 ml of 1.5 M solution of triethylaluminum (TEAL) (0.764 g, 0.0067 mol) in hexane, 3.4 ml of 0.1 M solution of t-butyl(4-methylpiperidyl)dimethoxysilane (0.0835 g, 0.0034 mol) of example 1 and allowed to stand for 5 minutes. Of this mixture, 35 ml was added to a flask. Then 0.0129 g of FT4S solid catalyst component (commercially available from HIMONT Italia S.r.l.) was added to the flask and mixed by swirling for a period of 5 minutes. The catalytic complex so obtained was introduced, under an argon purge, into the above polymerization reactor at room temperature. The remaining hexane/TEAL/silane solution was then drained from the addition funnel to the flask, the flask was swirled and the solution drained into the reactor.

The polymerization reactor was slowly charged with 2.2 liters of liquid propylene, while agitating, and 0.25 mole percent of $H_2$. Then the reactor was heated to 70° C. and maintained for about 2 hours at constant temperature and pressure. Agitation was then stopped and the remaining propylene was slowly vented. The reactor was heated to 80° C., purged with argon for 10 minutes and then cooled to room temperature and opened. The polymer was removed and dried in a vacuum oven at 80° C. for 1 hour.

The results of this polymerization run and other polymerization runs using the organosilane compound of example 1 carried out according to the procedure above, except for variations in the amounts thereof, are set forth in Table 2.

Unless otherwise specified, the intrinsic viscosity of the polymers, IV, is measured in decalin at 135° C. using a Ubbelohde type viscometer tube by the method of J. H. Elliott et al., J. Applied Polymer Sci., 14, 2947–63 (1970). The mileage of the polymer is calculated according to the formula:

$$\text{mileage} = \frac{\text{grams of polypropylene}}{\text{grams of catalyst}}$$

The percent xylene solubles at room temperature, % XSRT, of the polymer was determined by dissolving 2 g of polymer in 200 ml of xylene at 135° C., cooling in a constant temperature bath at 22° C. and filtering through fast filter paper. An aliquot of the filtrate was evaporated to dryness, the residue weighed and the weight % soluble fraction calculated.

TABLE 2

| $H_2$ % | Mileage g of PP/g of Cat. | IV | % XSRT |
|---|---|---|---|
| 0.00 | 21,000 | 11.80 | 3.67 |
| 0.10 | 33,600 | 4.43 | 1.79 |
| 0.15 | 35,800 | 4.50 | 1.83 |
| 0.25 | 42,800 | 3.96 | 1.93 |
| 0.30 | 54,800 | 3.31 | 1.41 |

Comparative polymerization runs were carried out according to the procedure above, but with diphenyldimethoxysilane (DPMS) and dicyclohexyldimethoxysilane in place of t-butyl(4-methylpiperidyl)dimethoxysilane used above. The results are given below in Table 3.

TABLE 3

| Electron Donor | $H_2$ % | Mileage g of PP/g of Cat. | IV | % XSRT |
|---|---|---|---|---|
| Diphenyl-dimethoxysilane | 0.00 | 25,000 | 6.28 | 4.73 |
| | 0.15 | 39,400 | 3.38 | 3.39 |
| | 0.30 | 41,100 | 2.55 | 2.43 |
| Dicyclohexyl-dimethoxysilane | 0.00 | 16,800 | 4.23 | 3.07 |
| | 0.30 | 32,400 | 3.05 | 2.90 |

It can be seen that the organosilane compound of the present invention in Table 2 when used as an electron donor with the co-catalyst component produced polymers having higher IV's and mileages with lower percentages of xylene soluble material as compared with the comparative electron donors of Table 3 used in the same manner.

Set forth below in Table 4 and 5 are results of polymerization runs using other organosilane compounds of the present invention and comparative electron donors. The polymerizations were carried out in the same manner as described above except for variations int he amounts thereof.

TABLE 4

| Organosilane Compound | $H_2$ % | Mileage g of PP/g of Cat. | IV | % XSRT |
|---|---|---|---|---|
| Ex. 4 | | | | |
| 2-Bicycloheptyl-(4-methylpiperidyl)dimethoxysilane (0.095 g, 0.335 mol) | 0.15 | 29,900 | 4.42 | 3.31 |
| | 0.35 | 35,700 | 3.90 | 3.33 |
| | 0.45 | 37,000 | 3.28 | 2.94 |
| Ex. 7 | | | | |
| Isopropyl-(4-methylpiperidyl)dimethoxysilane (0.078 g, 0.0335 mol) | 0.00 | 15,600 | 5.97 | 2.03 |
| | 0.30 | 36,100 | 3.59 | 1.29 |
| Ex. 9 | | | | |
| t-Butyl-(pyrrolidyl)-dimethoxysilane (0.073 g, 0.335 mol) | 0.00 | 20,700 | 4.10 | 1.52 |
| | 0.30 | 41,400 | 4.18 | 1.05 |
| | 0.50 | 48,400 | 3.54 | 1.51 |
| Ex. 10 | | | | |
| Heptamethylene-imine(methyl)-dimethoxysilane (0.073 g, 0.335 mol) | 0.30 | 38,200 | 2.30 | 1.34 |

TABLE 5

| Electron Donor | $H_2$ % | Mileage g of PP/g of Cat. | IV | % XSRT |
|---|---|---|---|---|
| Comparative Ex. 1 | | | | |
| 4-Methylpiperidine | 0.35 | 25,800 | 1.71 | 38.03 |
| Comparative Ex. 2 | | | | |
| Bis(dimethylamino) dimethylsilane | 0.35 | 17,700 | 2.10 | 19.10 |
| Comparative Ex. 3 | | | | |
| Phenyltriethoxysilane | 0.35 | 33,800 | 1.93 | 5.04 |

As demonstrated above, the organosilane compounds produced polymers having higher IV's and mileages along with lower percentages of xylene soluble material.

Other features, advantages and embodiments of the invention disclosed herein will be readily apparent to those exercising ordinary skill after reading the foregoing disclosures. In the regard, while specific embodiments of the invention have been described in considerable detail, variations and modifications of these embodiments can be effected without departing from the spirit and scope of the invention as described and claimed.

I claim:

1. Organosilane compounds of the general formula,

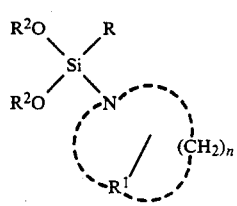

wherein R is a linear or branched $C_{1-4}$ alkyl, 4-methylpiperidyl, phenyl oplisually substituted in the para position with a halogen, $C_{1-4}$ linear or branched alkyl or alkoxy or $C_{5-7}$ cycloalkyl; $R^1$ is hydrogen, methyl or ethyl; $R^2$ is methyl or ethyl; and n is 4 to 7.

2. The compound of claim 1, wherein R is a linear or branched $C_{1-4}$ alkyl and n is 4.

3. The compound of claim 2 wherein R is t-butyl.

4. The compound of claim 1, wherein n is 5.

5. The compound of claim 4, wherein R is a linear or branched $C_{1-4}$ alkyl and R' is hydrogen or methyl.

6. The compound of claim 5 wherein R is isopropyl and $R^1$ is methyl.

7. The compound of claim 5 wherein R is t-butyl and $R^1$ is methyl.

8. The compound of claim 5 wherein R is n-butyl and $R^1$ is methyl.

9. The compound of claim 4 wherein R is 4-methylpiperidyl.

10. The compound of claim 4 wherein R is 2-bicycloheptyl.

11. The compound of claim 1 wherein n is 7 and R is a linear or branches $C_{1-4}$ alkyl.

12. The compound of claim 1 wherein n is 6 and R is a linear or branched $C_{1-4}$ alkyl.

* * * * *

UNITED STATES PATENT AND TRADEMARK OFFICE
CERTIFICATE OF CORRECTION

PATENT NO. : 5,166,340

DATED : November 24, 1992

INVENTOR(S) : Constantine A. Stewart

It is certified that error appears in the above-identified patent and that said Letters Patent is hereby corrected as shown below:

Col. 6, line 12, change "100" to --200--.

Col. 6, line 38, change "3" to --23--.

Col. 14, lines 20 and 21, change "2-bicycloheptyl" to

--2-bicyclo[2.2.1]heptyl--.

Signed and Sealed this

Seventh Day of December, 1993

Attest:

BRUCE LEHMAN

Attesting Officer

Commissioner of Patents and Trademarks